United States Patent [19]

LaHaye

[11] Patent Number: 5,031,622
[45] Date of Patent: Jul. 16, 1991

[54] DISPOSABLE ANTICONTAMINATION TONOMETER TIP COVER OR CAP

[75] Inventor: Peter G. LaHaye, Medina, Wash.

[73] Assignee: LaHaye Laboratories, Inc., Medina, Wash.

[21] Appl. No.: 500,790

[22] Filed: Mar. 28, 1990

[51] Int. Cl.$^5$ .............................................. A61B 3/16
[52] U.S. Cl. .................... 128/646; 128/652; 206/316.1; 206/363; 206/439; 206/471
[58] Field of Search ..................... 128/645–652, 128/736; 604/263; 206/69, 316.1, 363, 438, 439, 461, 471

[56] References Cited

U.S. PATENT DOCUMENTS

| | | | |
|---|---|---|---|
| 3,032,182 | 5/1962 | Bechtold | 206/439 |
| 3,507,386 | 4/1970 | Ishii et al. | 206/439 |
| 4,275,179 | 6/1981 | Sherman | 525/98 |
| 4,422,914 | 5/1990 | Segal et al. | 128/646 |
| 4,444,310 | 4/1984 | Odell | 206/363 |

OTHER PUBLICATIONS

Disposable Film Cover for the Tip of Goldmann's Tonometer, Nardi M; Bartolomei MP; Flaco L; Carelli F, Graefes Arch Clin Exp Ophthalmol 1985; 223 (2); 109–110.

Primary Examiner—Randy Citrin Shay
Attorney, Agent, or Firm—Gordon W. Hueschen

[57] ABSTRACT

A sterile disposable frustoconically-shaped plastic cover or cap adapted to fit over and be releasably and frictionally secured to the corresponding surfaces of a tonometer tip, having a planar lens portion at its smaller circumference adapted to lie against both the lens of the tonometer tip and against the cornea of the eye of a patient being examined with the tonometer, the lens portion of the cover being of optical clarity so as not to interfere with readings obtained with the tonometer, is disclosed. The cap includes peripheral slits for frictional and releasable securement of the cover about the surfaces of various-sized tonometer tips and external flanges for gripping the cover without contact with its lens portion, and is preferably constructed as a unitary device from a single plastic of optical clarity and packaged in the well of special packaging in which it is sterlized.

21 Claims, 2 Drawing Sheets

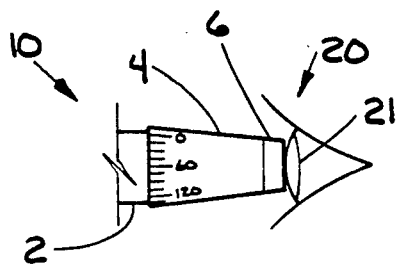
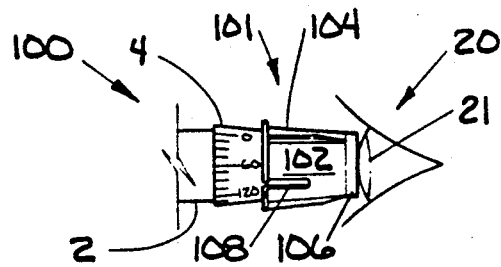
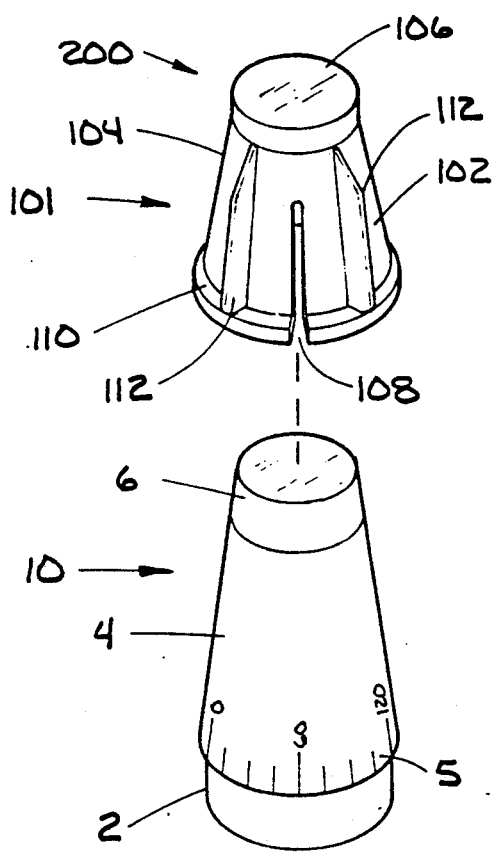
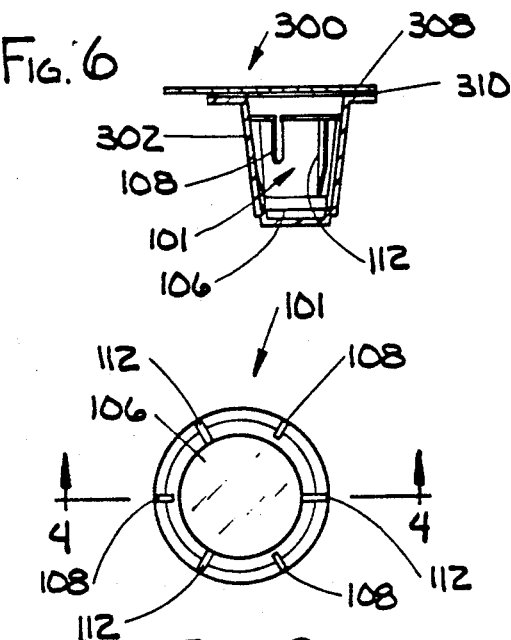
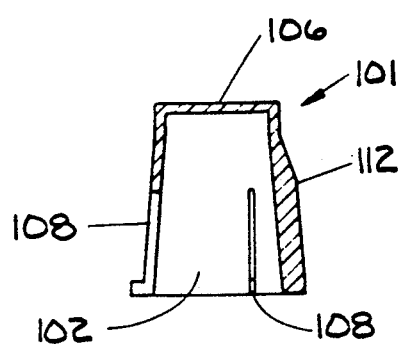

DISPOSABLE ANTICONTAMINATION TONOMETER TIP COVER OR CAP

BACKGROUND OF INVENTION

Field of Invention and Prior Art

Sterile disposable covers or caps for the tip of a tonometer, which is in practice pressed against the surface of the cornea of an eye, to prevent contamination of the cornea of a patient by transmission of contaminants such as bacteria or the like from one patient to the next during the normal employment of a tonometer.

Literally millions of tests to determine intraocular pressure indicative of glaucoma or related diseases of the eye, or tendencies thereto, are conducted yearly by opticians, optometrists, and their technical assistants. The device employed in the making of such observations is a tonometer. According to normal use of a tonometer, the operator of the same peers through the device and adjusts the lens at the end of the tip thereof against the cornea of the test subject in order to effect a specific diameter or circumference of a portion of the cornea which is flattened against the lens of the tonometer tip. When the necessary diameter or circumference of the area of flatness of the cornea against the lens has been attained, a blast of air is released against the flattened portion of the cornea, whereupon a reading is obtained which allows determination of the intraocular pressure within the eyeball.

In such a determination, the operator must be able to see through the lens of the tonometer tip in order to be certain that the necessary flattened area of the cornea for performance of the test has been attained, and calibrations are usually provided on the surface of a rotatable frustoconical-tonometer tip, which is rotatable upon a base member, for enabling the operator to make necessary adjustments in a particular case and e to enable a proper reading of the interocular pressure from employment of the device. The present invention has nothing to do with the normal operation of a conventional tonometer or tonometer tip, but seeks to provide a means for preventing transmittal of contamination of any kind, but most especially in the form of microorganisms such as bacteria or the like, from one patient to a succeeding patient during the normal course of tonometery examinations.

One of the foremost problems encountered in the use of a tonometer for such examinations is just the type of contamination mentioned. If one tested patient has a cornea which is contaminated with bacteria, and the lens of the tonometer tip is not adequately cleaned between employment of the device on succeeding patients, transmittal of the disease from one patient to a succeeding patient is not only likely, but in fact often occurs. The problem of adequately cleaning and sterilizing the lens of the tonometer tip between usage of the device upon a succession of patients is demanding and is often overlooked or inadequately carried out, so that it is not uncommon for a patient having recently undergone a tonometer test to develop "red eye", a bacterial and/or viral infection transmitted from one patient to another through the medium of contamination of or on the tonometer tip lens. This problem has been recognized and various review articles have appeared setting forth the problem, without however suggesting any practical solution thereto other than a more careful attention to the sterilization of the tonometer tip and/or more complete sterilization of the tonometer tip between its use on successive patients. Among some of the articles which have appeared are the following:

Viability of Herpes Simplex Virus Type 1 on the Applanation Tonometer, Ventura LM; Dix RD, *AM J Ophthalmol* 1987 Jan 15; 103 (1): 48–52.

"Sterilization of Impression Tonometers Using a Sterilization Ring. Virological Studies", Odkazanie tonometru impresvjnego przy uzyciu pierscienia sterylizacyjnego. Badania wirusologiczne, Jedrzejewski D; Gerkowicz M, *Klin Oczna* 1985 Aug; 87 (8): 315–317.

Disposable Film Cover for the Tip of Goldmann's Tonometer, Nardi M; Bartolomei MP; Falco L; Carelli F, *Graefes Arch Clin Exp Ophthalmol* 1985; 223 (2): 109–110.

Tonometer Disinfection and Viruses, Nagington J; Sutehall GM; Whipp P, *Br J Ophthalmol* 1983 Oct; 67 (10): 674–676.

"Septic Potential of Tonometers and Triple-mirror Glasses", Etude de la septicite des tonometres et des verres a trois miroirs, Rossazza C; Bertrand F; Vargues R, *Bull Soc Ophtalmol Fr* 1983 Mar; 83 (3): 411–412, 415–416.

"Modified Version of a UV Sterilizer to Disinfect Goldmann Tonometer Heads, Gonioscopes and Fundus Contact Lenses", Modifikation eines UV-Gerates zur Desinfektion bulbusberuhrender ophthalmologischer Instrumente, Wizemann A, *Klin Monatsbl Augenheilkd* 1982 Jul; 181 (1): 40–41.

Hepatitis B Surface Antigen in Human Tears, Darrell RW; Jacob GB, *Arch Ophthalmol* 1978 Apr; 96 (4): 674–676.

Contamination of Applanation Tonometer Prism, Norn MS; Thomsen F, *Acta Ophthalmol* (Copenh) 1968; 46 (4): 712–720.

The problem is widespread and has been particularly recognized in the Nardi et al. publication entitled "Disposable Film Cover for the Tip of Goldmann's Tonometer", appearing in Graefe's Archive of Clinical and Experimental Ophthomology, cited in the foregoing, but the proposal advanced by those authors is unacceptable in practice and leaves much to be desired. In their proposal, a drop of distilled water must be placed on the front surface of the double prism of the tonometer, and a polyvinyl chloride (PVC) film disk, fixed to a circular rigid mount and perforated about its internal circumference, must then be held by the mount and pressed against the front surface of the double prism in order to apply an even film of liquid between the PVC film and the double prism itself. Then, by further traction and a twisting movement on the mount, the film is torn at the level of the perforations, and caps the double prism with a thin transparent film, whereafter the tonometer tip or prism can be remounted on the tonometer. After employment in tonometry, the film must then be removed with forceps. Care must be taken so as not to impair its sterility, especially before use. This proposed solution to the problem is, however, much too complex and delicate for practical use and the major contribution of this article is to point up the problem of sterility with the tonometer tip and the prism located therein, which is the problem solved by the device of the present invention. According to Nardi et al., the methods previously suggested for solution of the problem have at least one of the following drawbacks: (1) they are unreliable, especially in the case of viral infection; (2) they are not practical; (3) they are time consuming; (4) they can damage the double prism (citing additional publications). Nardi's proposal falls in at least category (2).

It would, accordingly, be highly desirable to have available an economical and readily-utilizable means for ensuring that the portion of the tonometer which comes into contact with the cornea of the eye of a patient being tested therewith is sterile and free from contamination, especially due to use of the tonometer upon a preceding patient, and the present invention provides just such a means in the form of a disposable anticontamination tonometer tip cover or cap, which does not in the slightest interfere with the normal operation of the tonometer but which, on the other hand, not only avoids the tedious problem of sterilization and adequate sterilization of the lens of the tonometer tip between patients, but moreover provides a practical and use-effective means for ensuring sterility of the portion of the tonometer which comes into contact with the cornea of every patient tested therewith.

OBJECTS OF THE INVENTION

It is accordingly an object of the present invention to provide a disposable anticontamination tonometer tip cover or can, which has a sterile cornea-contacting section and which accordingly ensures sterility of the portion of the tonometer device which comes into contact with the cornea of a patient being examined therewith. Another object is the provision of such a device which is readily adaptable to employment with varying sizes of tonometer tips which are employed on or as a part of various conventional tonometers. A further object of the invention is the provision of such a cover or cap device which has a lens portion of crystal clarity or transparency so that, when it is placed on the tonometer tip, in contact with the lens of the tonometer, the tonometer calibration or reading is not altered or impaired. An additional object of the invention is the provision of such a device which is finger-grippable by the operator and readily and releasably friction-securable about the circumference of a normal and usual tonometer tip. Still an additional object of the invention is the provision of such a sterile device in particular and special packaging therefor, which enables the packing of the device of the invention therein in a manner which requires contact of only a minimal, if any, segment of the lens portion thereof with the packaging itself, and which is readily grippable by the fingers of the operator for ready removal, without contamination, of the cover or cap of the invention from its sterile packaging. Still an additional object of the invention is the provision of such a tonometer tip cover or cap in special packaging and enclosed therein by means of a conveniently-removable cover sheet which is gas-permeable, thereby enabling the placement of the cover or cap of the invention into its special packaging and subsequent sterilization thereof in situ, as by irradiation or ethylene oxide or like gaseous sterilizing agent, for further ensuring sterility of the cornea-contacting portion of the device of the invention.

Still other objects of the invention will be apparent to one skilled in the art and still additional objects will become apparent as the description proceeds.

SUMMARY OF THE INVENTION

The invention, then, comprises the following aspects, inter alia, singly or in combination:

A disposable plastic frustoconically-shaped cover or cap adapted to fit over and to be frictionally but releasably secured to corresponding frustoconical surfaces of a tonometer tip, having frustoconical walls and a planar lens portion at the smaller circumference thereof adapted to abut the lens means of a tonometer tip when assembled thereon as well as to lie against the cornea of the eye of a patient being examined with the tonometer instead of the lens means of the tip of the tonometer itself, at least the lens portion of the cover or cap being of optical clarity so as not to interfere with readings obtained with the tonometer, the frustoconical walls of said cover or cap being provided with means to enable the frictional but releasable securement of said cover or cap about the frustoconical surfaces of the tonometer tip; such a device wherein said frictional and releasable securement means comprises expansion means for frictional but releasable securement of said cover or cap about the frustoconical surfaces of various-sized tonometer tips; such a device comprising external finger-grippable means in the walls thereof for gripping of said cover or cap without contact with the lens portion thereof; such a device wherein said expansion means are provided in the form of slits; such a device wherein said finger-grippable means are provided in the form of flanges, ridges, or ribs; such a device wherein a strengthening and supporting flange is provided around the circumference of the frustoconical wall of said cover or cap at or near the end thereof opposite to the lens portion thereof; such a device which is constructed as a unitary device from a single clear plastic; such a device wherein the plastic is a styrene-butadiene coploymer; such a device which is formed by injection molding; such a device in sterile condition; such a device sterilized by means of ethylene oxide gas; such a device packaged in the well of a sterilizable package comprising a well having a top and bottom and having frustoconical walls corresponding to the frustoconical walls of the device, with the largest circumferences of the well and the device being upwardly disposed, and a sheetform cover member removably adhered to the top of said well, whereby removal of the cover member permits access to the interior of the well of the package and removal of the device without contacting the lens portion thereof; such a packaged device comprising finger-grippable means in the walls thereof for gripping of said device without contact with the lens portion thereof and wherein said frictional and releasable securement means comprises expansion means for frictional but releasable securement of said cover or cap about the frustoconical surfaces of various-sized tonometer tips; such a device wherein the package comprises an inwardly-extending protuberance which is provided toward the bottom of said well for support of said device thereon without contacting a substantial segment of the lens portion of said device; such a device wherein said protuberance is provided in the form of a supporting ledge around the circumference of said well, thereby providing support for said device within said well around the circumference of the lens portion thereof; such a device wherein said package cover member is gas-permeable and wherein the interior of said package is in sterile condition as sterilized by subjection to a gaseous sterilization cycle; such a device wherein said package cover member is ethylene oxide-permeable and wherein the interior of said package is in sterile condition as sterilized by subjection to an ethylene oxide sterilization cycle; such a device wherein the cover member is sealed to the upwardly-disposed end of the frustoconical well of the package; such a device wherein the cover member is heat-sealed to flanges located at the upwardly-disposed end of the frustoconical well of the package; and such a device wherein the cover member comprises a plastic-coated paper.

THE DRAWINGS

Reference is now made to the drawings for a better understanding of the invention, wherein:

FIG. 1 is a schematic view of the tonometer tip of a conventional tonometer showing the lens thereof placed against the cornea of the eye of a patient being examined therewith.

FIG. 2 is the same as FIG. 1 with the exception that the tonometer tip cap or cover of the invention is shown in place between the tonometer tip and the cornea of the eye.

FIG. 3 is a top view of a tonometer tip cover or cap according to the invention.

FIG. 4 is a cross-sectional view taken on the line 4—4 of FIG. 3.

FIG. 5 is an isometric view of a tonometer tip with the tonometer tip cap or cover of the invention in position to be pressed into place about the circumference thereof, as shown in FIG. 2.

FIG. 6 is a sectional view of a device of the invention in place within its special packaging, an enlargement of which appears in FIG. 8.

DETAILED DESCRIPTION OF THE INVENTION

Figure 7:
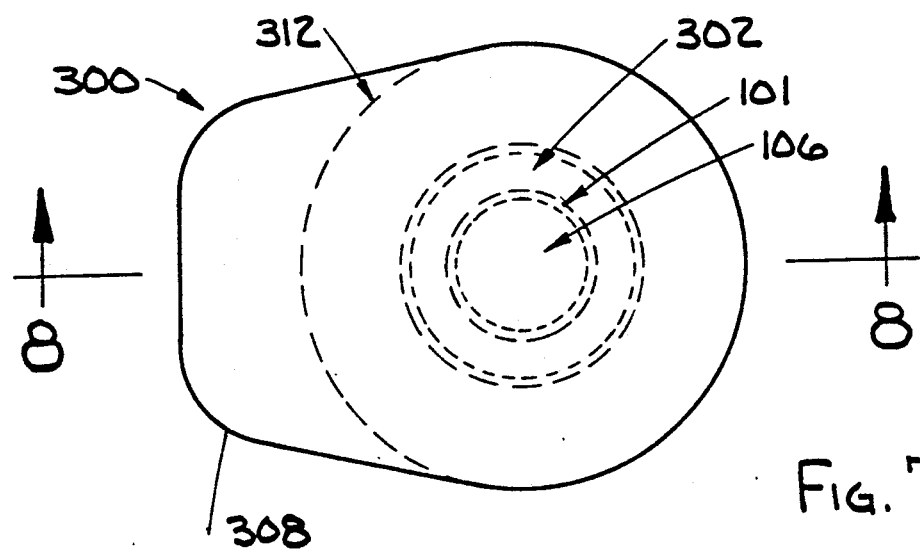
FIG. 7 is a top view of a device of the invention in place in the special packaging therefor, everything interior of the packaging being shown in shadow lines.

Referring now to the drawings, wherein the same numbers or numbers differing by factors of ten or one hundred are used to illustrate the same elements throughout, FIG. 1 at 10 generally shows the tonometer tip of a conventional tonometer assembly in use.

The tonometer tip 4 is of a generally frustoconical shape and is rotatably mounted on base member 2 and comprises lens member 6 which, as shown, is the portion thereof coming into contact with cornea 21 of the patient's eye 20 during testing.

In FIG. 2 at 100 is shown the same tonometer tip but modified by the disposable anticontamination tonometer tip cover or cap of the present invention, as shown at 101 also having a generally frustoconical shape corresponding to that of the tonometer tip itself and slipped into place thereover, where it is held by friction. Tonometer tip cover or cap proper 104 comprises frustoconical wall section 102 in turn comprising expansion means in the form of slits 108 as well as external gripping means in the form of flanges 112 and the essential clear lens portion 106 which, as shown, now comes in contact with cornea 21 instead of lens means 6 of the tonometer tip proper 4.

From FIG. 3 are better seen clear lens means 106, expansion means in the form of slits 108, and external gripping means in the form of ridges, ribs, or flanges 112, all in the frustoconical wall 102 of cover or cap proper 104.

The same elements are visible in the cross sectional view of FIG. 4.

FIG. 5 shows at 200 an exploded and enlarged view of the assembly of FIG. 2, including the tonometer tip assembly 10 comprising the elements previously described, having a frustoconical shape and embodying lens portion 6, rotatable frustoconical cone 4 bearing calibrations 5, rotatably mounted on base 2, all as present in a conventional tonometer for normal use by the operator. Superimposed above the conventional tonometer tip assembly 10, ready to be slidably and frictionally but releasably secured thereover by the operator, where it will be held by surface friction, is the cover or cap 101 of the invention. In effecting the further assembly of FIG. 2, the operator merely grips cap or cover 101 by external gripping means 112, as shown in the form of a flange, ridge, or rib. The cap or cover 101 is readily slipped over the frustoconical walls of tonometer tip 4, where it is securely but releasably secured by friction and pressure as conveniently provided by expansion means 108 in the form of slits included for such purpose. At least lens portion 106 of cap or cover 101 is of clear plastic but, as shown, cap or cover 101 is preferably and advantageously provided in the form of an integral plastic pressure- or injection-molded unit, all of which is of crystal clarity and good impact strength. For this purpose, any injectable or moldable plastic material may be employed, so long as it is of sufficient clarity as not to interfere at the lens portion 106 thereof with the operativeness of the lens means 6 of the tonometer tip proper, against which it will lie in close juxtaposition, with essentially no space therebetween, as shown in FIG. 2. For this purpose a copolymer of butadiene and styrene known as a "K-resin"(TM), from Phillips Petroleum, is preferred, although crystal clear polystyrenes, such as available from Huntsman, Calibre(TM) polycarbonate resins available from Dow, as well as Cyrolite(TM) and Acrylite (TM) molding and extrusion compounds from Cyro Industries, may be employed with equal or nearly equal facility, as long as the particular plastic is selected to have sufficient impact strength and clarity. At least the clear cornea-contacting lens portion 106 formed therefrom, and which is placed in touching or abutting contact with lens means 6 of the tonometer tip proper 4, must of necessity be of sufficient clarity so as not to interfere with operativeness of the tonometer device, for which it provides a "second window". The plastic employed for the cover or cap 101 of the invention, and especially at least the clear cornea-contacting lens means 106 thereof, must accordingly be of optical quality clear plastic and lens portion 106 of the device must be essentially what is commonly referred to as an optically-clear or "plano" lens.

After the operator has slidably and frictionally but releasably engaged and secured the cap or cover 101 of the invention about the frustoconical tonometer tip 4 using finger-grip means in the form of flanges, ridges, or ribs 112, the assembly is in the form shown in FIG. 2. As shown in FIG. 5, the cover or cap 101 of the invention may advantageously also comprise bottom flange 110, which is preferred for strength and stability, but which may be dispensed with in certain embodiments.

For packaging of the cover or cap 101 of the invention, the device is advantageously inserted into special sterilizable packaging as shown at 300 in FIG. 6, wherein the device 101 of the invention may be sterilized by any non-destructive procedure, such as gaseous permeation or irradiation sterilization. A top view of the packaging, with the cover or cap 101 of the invention in place therein, is shown in FIG. 7, from which the sheetform cover 308 is clearly seen and the position of the essential elements, especially lens portion 102, of the cover or cap 101 of the invention, as previously described, as well as package well flange 312 and outer wall 302 of the package well 304 may be seen in phantom lines.

Figure 8:
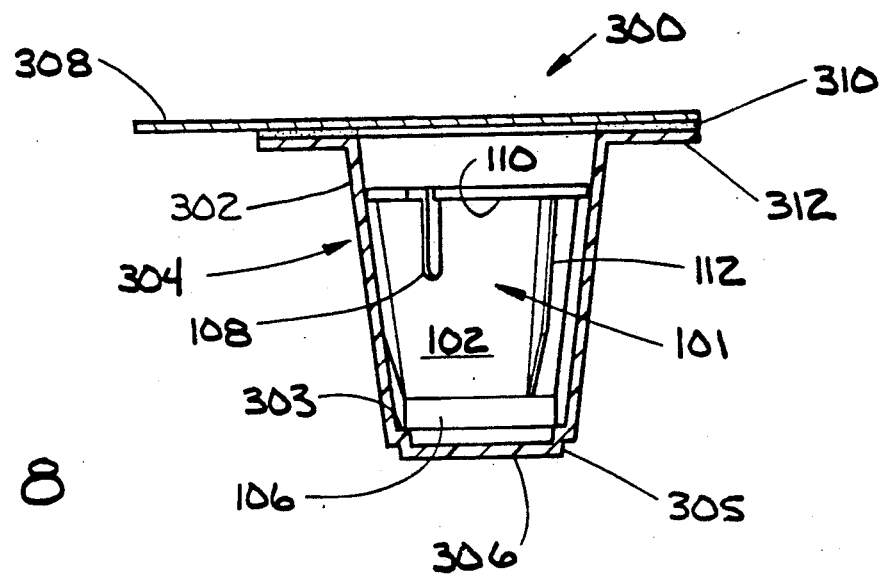
FIG. 8 is a cross-sectional view along the line 8—8 of FIG. 7, being an enlargement of FIG. 6 for purposes of better illustrating the details thereof.

As shown in the enlarged version of FIG. 6 identified as FIG. 8, the special packaging involves inverted or downwardly-tapering frustoconical well 304 having walls 302 terminating in outwardly-extending flange 312 to which gas-permeable sheetform cover or closure member 308 is adhesively secured by adhesive 310 in the usual manner for such packaging, which may be in either single or multiple unit configuration. As shown, at or near the bottom 306 of frustoconical well 304 is located inwardly-disposed circular protuberance 305 of slightly diminished circumference. This provides internal supporting ledge 303, for support of the outwardly-disposed external edges of clear lens portion 106 of the cover or cap 101 of the invention thereon. Alternatively, such supporting ledge may be provided in the form of inwardly-extending protuberances (not shown) which need not extend completely around the circumference of well 302 at or near the bottom thereof. From FIG. 8, the other already-enumerated essential elements of the cap or cover 101 of the invention are readily seen. The wall 302 of package 300 is of plastic of usual type, such as polyethylene, polystyrene, polypropylene, or any of the plastics previously mentioned for construction of the cover or cap proper, the foremost considerations in this regard being sterilizability and economy. For the sheetform cover or closure member 308, any suitable material may be employed, such as of paper, paperboard, foil, plastic, or plastic-coated paper, the uncoated Tyvek(TM) sheetform lid material from Baxter Health Care Corporation, Pharmaseal Division, being one suitable closure-forming material, but coated Tyvek(TM), a medical-grade heat-seal coated Tyvek(TM), which is capable of withstanding normal gaseous, i.e., ethylene oxide, sterilization cycles, also from Baxter, being much preferred. In such case a heat-sealing adhesive or thermoplastic material 310 is coated directly upon the material of the closure or cover member 308 so that the use of a separate or independent adhesive 310 may be dispensed with and the coated cover or closure 308 heat-sealed directly to the laterally-extending flange 312 located at the upwardly-disposed end of the walls 302 of frustoconical well 304. The same is true when the cover member 308 is itself of a heat-sealable thermoplastic material.

After packaging, the device of the invention is subjected to sterilization in the package according to usual procedure in the art, as by subjection to irradiation or a gaseous sterilization cycle, preferably an ethylene oxide sterilization cycle, to produce a completely sterile tonometer tip cover or cap within its packaging. The efficiency of gaseous sterilization cycles is greatly facilitated by the employment of packaging material which is gas-permeable, especially for the cover or closure member of the package, as previously set forth in the foregoing.

Other materials which are obvious equivalents of the plastics or other materials employed for production of the tonometer cover or cap 101 of the present invention, of the well 304 of the package of the invention, and of the cover- or closure-forming material for package cover member 308 will immediately be apparent to one skilled in the plastics and packaging arts, and numerous thereof are available which are full equivalents of those preferred embodiments specifically set forth in the foregoing.

It is accordingly seen that the present invention provides an important sterile cover or cap for tonometer tips which embodies, at least in the lens and cornea-contacting portion thereof, an optically or crystal clear plastic lens material which does not interfere with operation of the tonometer itself, which is readily adaptable to functionally engage various-sized tips of various tonometers, which is economical and disposable, and which eliminates the necessity for direct contact of the lens means of a conventional tonometer tip with the cornea of a patient undergoing an eye examination therewith, thereby also obviating the possibility of transmittal of contamination of any type, but especially viral, bacteriological, or other microbiological infection, from one patient to a subsequent patient being subjected to examination with the same tonometer device.

Although the preferred embodiments of the invention have been illustrated in the accompanying drawings and described in the foregoing description, it is to be understood that the invention is not limited to the embodiments disclosed or to the exact details of operation or exact compounds, compositions, methods or procedures shown and described, since the invention is capable of numerous modifications, rearrangements, and substitutions of parts and elements and other equivalents, both physical and mechanical, without departing from the spirit or scope of the invention, as will be readily apparent to one skilled in the art, so that the present invention is to be understood as being limited only by the full scope which can be legally accorded the appended claims.

I claim:

1. A disposable plastic frustoconically-shaped cover or cap, adapted to fit over and to be frictionally but releasably secured to corresponding frustoconical surfaces of a tonometer tip, having frustoconical walls and a planar lens portion at the smaller circumference thereof adapted to abut lens means of a tonometer tip when assembled thereon as well as to lie against the cornea of the eye of a patient being examined with the tonometer, instead of the lens means of the tip of the tonometer itself, at least the lens portion of the cover or cap being of optical clarity so as not to interfere with readings obtained with the tonometer, the frustoconical walls of said cover or cap being provided with expansion means for frictional but releasable securement of said cover or cap about the frustoconical surfaces of various sized tonometer tips, said expansion means being provided in the form of slits.

2. The device of claim 2, comprising external finger-grippable means in the walls thereof for gripping of said cover or cap without contact with the lens portion thereof.

3. The device of claim 2, wherein said finger-grippable means are provided in the form of flanges, ridges, or ribs.

4. The device of claim 2, wherein a strengthening and supporting flange is provided around the circumference of the frustoconical wall of said cover or cap at or near the end thereof opposite to lens portion thereof.

5. A device of claim 2, which is constructed as a unitary device from a single clear plastic.

6. The device of claim 5, wherein the plastic is a styrene-butadiene coploymer.

7. The device of claim 5, in sterile condition.

8. The device of claim 1, in sterile condition.

9. The device of claim 1, packaged in a well of a sterilizable package comprising a well having a top and bottom and having frustoconical walls corresponding to the frustoconical walls of the device, with the largest circumferences of the well and the device being upwardly disposed, and a sheetform cover member removably adhered to the top of said well, whereby removal of the cover member permits access to the interior of the well of the package and removal of the device without contacting the lens portion thereof.

10. The device of claim 9, wherein the packaged device comprises finger-grippable means in the walls thereof for gripping of said device without contact with the lens portion thereof and wherein said frictional and releasable securement means comprises expansion means for frictional but releasable securement of said cover or cap about the frustoconical surfaces of various-sized tonometer tips.

11. The device of claim 10, which is constructed as a unitary device from a single clear plastic.

12. The device of claim 9, wherein the package comprises an inwardly-extending protuberance which is provided toward the bottom of said well for support of said device thereon without contacting a substantial segment of the lens portion of said device.

13. The device of claim 12, wherein said protuberance is provided in the form of a supporting ledge around the circumference of said well, thereby providing support for said device within said well around the circumference of the lens portion thereof.

14. The device of claim 9, wherein the interior of said package is in sterile condition.

15. The device of claim 14, wherein the cover member is sealed to the upwardly-disposed end of the frustoconical well of the package.

16. The device of claim 15, wherein the cover member is heat-sealed to a flange located at the upwardly-disposed end of the frustoconical well of the package.

17. The device of claim 15, wherein the cover member comprises a plastic-coated paper.

18. The device of claim 9, wherein said package cover member is gas-permeable and wherein the interior of said package is in sterile condition as sterilized by subjection to a gaseous sterilization cycle.

19. The device of claim 18, wherein said package cover member is ethylene oxide-permeable and wherein the interior of said package is in sterile condition as sterilized by subjection to an ethylene oxide sterilization cycle.

20. A disposable plastic frustonconically-shaped cover or cap, adapted to fit over and to be frictionally but releasably secured to corresponding frustoconical surfaces of a tonometer tip, having frustoconical walls and a planar lens portion at the smaller circumference thereof adapted to abut lens means of a tonometer tip when assembled thereon as well as to lie against the cornea of the eye of a patient being examined with the tonometer, instead of the lens means of the tip of the tonometer itself, at least the lens portion of the cover or cap being of optical clarity so as not to interfere with readings obtained with the tonometer, the frustoconical walls of said cover or cap being provided with means to enable the frictional but releasable securement of said cover or cap about the frustoconical surfaces of the tonometer tip, said device being packaged in a well of a sterilizable package comprising a well having a top and bottom and having frustoconical walls corresponding to the frustoconical walls of the device, with the largest circumferences of ht well and the device being upwardly disposed, ar.d a sheetform cover member removably adhered to the top of said well, whereby removal of the cover member permits access to the interior of the well of the package and removal of the device without contacting the lens portion thereof, wherein the package comprises an inwardly-extending protuberance which is provided toward the bottom of said well for support of said device thereon without contacting a substantial segment of the lens portion of said device.

21. The device of claim 20, wherein said protuberance is provided in the form of a supporting ledge around the circumference of said well, thereby providing support for said device within said well around the circumference of the lens portion thereof.

* * * * *

UNITED STATES PATENT AND TRADEMARK OFFICE
CERTIFICATE OF CORRECTION

PATENT NO. : 5,031,622

DATED : Jul. 16, 1991

INVENTOR(S) : Peter G. LaHaye

It is certified that error appears in the above-identified patent and that said Letters Patent is hereby corrected as shown below:

```
Title Page, [56] References Cited, U.S. PATENT DOCUMENTS,
    fourth line; "4,422,914" should read -- 4,922,914 --.
Column 1, line 38; "e to" should read -- to --.
Column 3, line 41; "mometer" should read -- nometer --.
Column 8, line 65; "claim 2," should read -- claim 1 --.

Column 9, approximately line 12; "copolymer" should read
    -- copolymer --.
Column 10, line 15; "frustonconically" should read
    -- frustoconically --.
Column 10, line 34; "ht" should read -- the --.
```

Signed and Sealed this

Twenty-second Day of December, 1992

*Attest:*

DOUGLAS B. COMER

*Attesting Officer*   *Acting Commissioner of Patents and Trademarks*